United States Patent [19]

Hewson

[11] Patent Number: 5,052,390

[45] Date of Patent: Oct. 1, 1991

[54] METHOD AND APPARATUS FOR DEFIBRILLATING THE HEART USING INTERNAL ESOPHAGEAL ELECTRODE AND EXTERNAL CHEST ELECTRODE

[76] Inventor: Carl E. Hewson, Old Ocean St., Marshfield, Mass. 02050

[21] Appl. No.: 214,778

[22] Filed: Jul. 5, 1988

[51] Int. Cl.⁵ ............................................. A61N 1/39
[52] U.S. Cl. ................................ 128/419 D; 128/786
[58] Field of Search ............ 128/419 D, 419 PG, 786

[56] References Cited

U.S. PATENT DOCUMENTS

| | | | |
|---|---|---|---|
| 4,198,963 | 4/1980 | Barkalow et al. | 128/802 |
| 4,574,807 | 3/1986 | Hewson et al. | 128/419 PG |
| 4,640,298 | 2/1987 | Pless et al. | 128/419 D |
| 4,706,688 | 11/1987 | Don Michael et al. | 128/419 D |

Primary Examiner—William E. Kamm
Assistant Examiner—Scott M. Getzow

[57] ABSTRACT

When the heart is in ventricular fibrillation, the heart cells that stimulate the heart muscles produce rapid repetitive excitation without coordinated contraction of the ventricle. There is no effective simultaneous action to make the heart beat in a ryhthmic fashion. A defibrillator delivers to the heart cells and muscles, enough voltage to override the erratic voltages in the heart (called repolarization) so they can rearrange themselves with order. The heart can then start over to deliver a regular rhythm.

Atrial defibrillation is achieved with an internal esophageal electrode and an external chest electrode placed approximately on a line between the two nipples and part way between the sternum and the left nipple. This provides a precise path for the defibrillating pulse and consequently a very efficient path, so that defibrillation is accomplished with very low power of 30 to 70 joules (average 50 joules) compared to what is normally used, namely, 100 to 360 joules.

Also in accordance with this invention, ventricular defibrillation is achieved with an internal esophageal electrode and an external chest electrode placed approximately over the apex of the left ventricle. This provides a precise path for the defibrillating pulse, and consequently a very efficient path so that the power of the same magnitude as those used for atrial defibrillation are used for ventricular defibrillation.

8 Claims, 4 Drawing Sheets

METHOD AND APPARATUS FOR DEFIBRILLATING THE HEART USING INTERNAL ESOPHAGEAL ELECTRODE AND EXTERNAL CHEST ELECTRODE

RELATED APPLICATION

This application is directed to an improvement of the electrode placement disclosed in Applicant's U.S. Pat. No. 4,735,206 issued Apr. 5, 1988 and entitled "Method And Apparatus for Defibrillating and Pacing the Heart".

FIELD OF THE INVENTION

This invention relates to a method of defibrillating the heart.

BACKGROUND OF THE INVENTION

There are two types of heart fibrillation, namely, ventricular and atrial fibrillation.

When a person's heart is in ventricular fibrillation, death is imminent. In ventricular fibrillation, the heart cells that stimulate the heart muscles are not coordinated so that although they stimulate the muscles, they produce rapid, erratic excitation without coordinated contraction of the ventricle. There is no effective simultaneous action to cause the heart to beat in rhythmic fashion. To avoid death, immediate defibrillation is essential.

When a person's heart is in atrial fibrillation, the atria are uncoordinated and are not beating in a rhythmic fashion. Atrial fibrillation generally is not life threatening. Atrial fibrillation with a clinically stable patient may be resolved with drug therapy, and when necessary, with electrical fibrillation. If atrial defibrillation is coupled with rapid ventricular response and other medical problems, it may be necessary to perform emergency electrical defibrillation.

Defibrillation is achieved by delivering to the heart cells enough voltage to override the erratic voltages in the fibrillating heart so that they can rearrange themselves with order. That action is called "repolarization". In this "repolarized" condition no heart action of any kind occurs for a period of three to eight seconds. After this three to eight seconds period, the heart cells arrange themselves to either fibrillate again or start a coordinated effort to beat in rhythm. If they fibrillate again, it is necessary to defibrillate them again, usually with more power. It may be necessary to do this several times before the heart cells arrange themselves to coordinate and beat in rhythm.

Defibrillation by high power is the accepted procedure today. Heavy duty equipment is required to deliver a very severe electric shock to the patient. The shock is delivered by placing two large paddle-type electrodes, each about three inches in diameter, at selected locations on the chest. By pressing down hard on the electrodes to make good electrical contact with the skin, and by pressing a button provided on one of the paddle electrodes, the system is triggered so as to deliver the shock. The electrical shock is very abrupt; several thousand volts are impressed across the electrodes in a few milliseconds. In accordance with this procedure, in theory if the patient is given a large enough shock, some of it will pass though the heart and achieve repolarization. However, all the other muscles and nerves in the large area between the electrodes are also stimulated by the intense electrical shock, causing tremendous body flailing and thrashing. The power required for this type of defibrillation is a minimum of 100 joules; sometimes 200 joules are required, and usually 360 joules are necessary.

SUMMARY OF THE INVENTION

In my earlier U.S. Pat. No. 4,735,206 supra, a method and apparatus are disclosed which uses an internal electrode in the esophagus and an external electrode on the chest, and a special pulse form is prescribed, which rises from zero to a selected value of not more than 150 volts in approximately three-tenths of a second. Further research has revealed that different and precise locations for the external electrode for treating the different kinds of fibrillation produce improved results over the results achieved with the use of the invention in U.S. Pat. No. 4,735,206, and they enable the use of conventional defibrillator energy sources. All conventionally used defibrillators are composed of two parts. The first part houses all the electronics to deliver the electrical shock. The second part is the electrodes which deliver the shock to the patient and are placed on the body of the patient.

The need is to use the smallest amount of power to the patient to accomplish defibrillation as it is the least abusive to the patient. The emphasis has been placed on electrical wave shape to achieve efficiency and thereby reduce the power necessary for defibrillation.

I have completely changed the delivery system to the patient to achieve a tremendous difference in efficiency so that only 1/5 to 1/9 the power previously used is required. This is done regardless of electrical wave shape.

By careful precise location of the electrodes, one in the lower esophagus and the other on the chest, this efficiency is achieved. And as with my earlier invention, the abusive effects of high voltage, high power techniques of defibrillation are avoided.

In accordance with the present invention, two small intimately located electrodes are used. In the case of atrial defibrillation, one electrode is located in the lower esophagus intimate to the posterior section of the heart and the other small electrode is placed on the chest approximately on a line between the two nipples and part way between the sternum and the left nipple. In the case of ventricular defibrillation, one electrode is located in the lower esophagus intimate to the posterior section of the heart and the other small electrode is placed on the chest approximately over the apex of the left ventricle. The placement of the electrodes provides a precise electrical path through the heart as selected by the location of the chest electrode, depending on whether atrial or ventricular defibrillation is required.

Because the selected path is precise, defibrillation with the first shock is assured, a minimum amount of extraneous muscle action occurs, and most importantly the power required is at a minimum of 30 to 70 joules, usually at the 50 joule level. This is equivalent to the power commonly used for internal defibrillation.

The internal electrode in the esophagus may be inserted through the mouth in the fashion of a gastric tube. The electrode itself may be of selected stiffness and flexibility so that it can be inserted directly into the esophagus. In the preferred embodiment, the electrode carries a plurality of circular contacts provided in the surface of the lower end of the tube. A stop may be carried on the other end of the electrode which will engage the face of the patient so as to prevent further electrode insertion when the distal end is in the proper location. In another embodiment, we have an internal electrode which may be inserted through the nasal passage into the esophagus. This will be of selected stiffness and flexibility. A stop may be carried on the other end of the electrode which will engage the nares of the patent so as to prevent further electrode insertion when the distal end is in the proper location. The external electrode may be an adhesively attached electrode as is commonly used for EKG, etc.

Because of the reduction in energy (joules) needed, the defibrillation unit may be reduced in size. The reduction in size may be quite remarkable because the components in most defibrillators—the large capacitor, the batteries to charge the capacitor, the rectifiers to recharge the batteries, and the relay to discharge the capacitor to the electrodes, are all heavy duty electrical equipment. By reducing the power needed, these may be reduced in size and weight and may be of solid state electronic components instead of electrical components. The size and weight of the defibrillator unit may be reduced to $\frac{1}{4}$ to $\frac{1}{3}$ the size and weight of the units now used to deliver 30-360 joules.

The present invention will be better understood and appreciated from the following detailed description read in connection with the accompanying drawings.

DETAILED DESCRIPTION OF THE INVENTION

Figure 1:
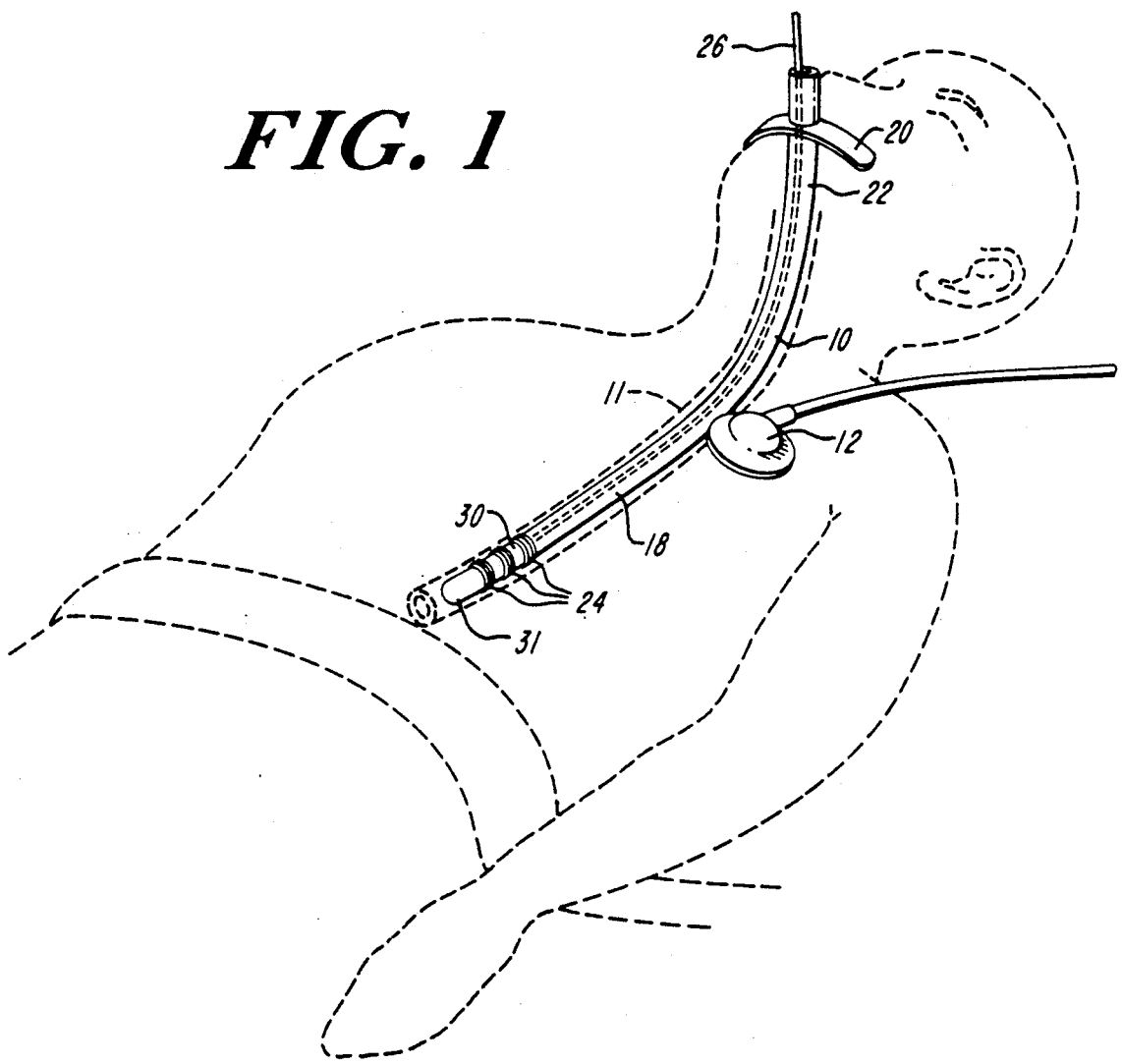
FIG. 1 is a somewhat diagrammatic view, of the head and chest of a patient and showing the use of the present invention.

FIG. 1 depicts a patient being assisted by the defibrillating system of the present invention. A first electrode 10 is shown disposed in the patient's esophagus 11, and an external electrode 12 is shown placed on the patient's chest. The electrodes are connected to an electrical circuit 16 shown in FIG. 6 which impresses a pulse across the electrodes 10 and 12 so as to instantaneously direct current through the heart.

Figure 4:
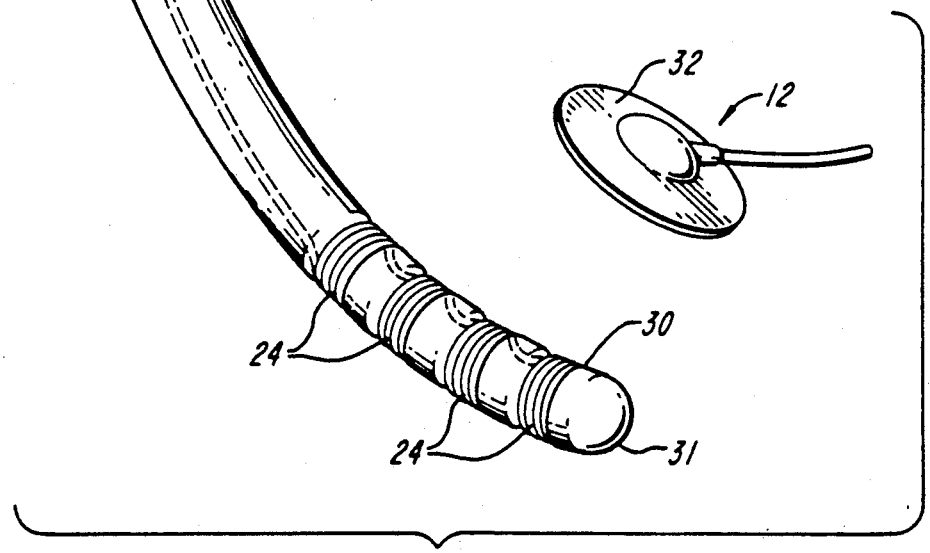
FIG. 4 is a perspective view of the two electrodes used to perform defibrillation in accordance with the present invention.

In FIGS. 1 and 4, the electrode 10 is shown to include a curved, tubular body 18 which is shaped to be inserted directly into the patient's esophagus without the aid of a larger tubular member serving as a guide for that purpose. It is to be understood, however, that the system of the present invention may be used in combination with other apparatus, and it is contemplated that the electrode 10 in certain situations may be guided into the esophagus through a previously inserted tube such as a gastric tube. The electrode 10 carries a stop 20 at its proximal end 22 which may be used to limit the depth of penetration of the electrode 10 into the esophagus. The stop 20 should not cover the mouth or otherwise interfere with the passage of air to and from the lungs.

The body of the electrode 10 preferably is somewhat flexible, in the nature of a commercially available gastric tube, so that it may be inserted in the esophagus and will not injure the esophageal lining. It may or may not call for the use of lubricant. Moreover, the electrode may be inserted through the mouth or nose. The electrode may be identical to that shown in U.S. Pat. No. 4,574,807 dated Mar. 11, 1988 and entitled "Method and Apparatus for Pacing the Heart Employing Internal and External Electrodes". The present applicant is a coinventor in that patent. The electrode is also shown in applicant's U.S. Pat. No. 4,683,890 dated Aug. 4, 1987 and entitled "Method and Apparatus for Controlled Breathing Employing Internal and External Electrodes".

Figure 5:
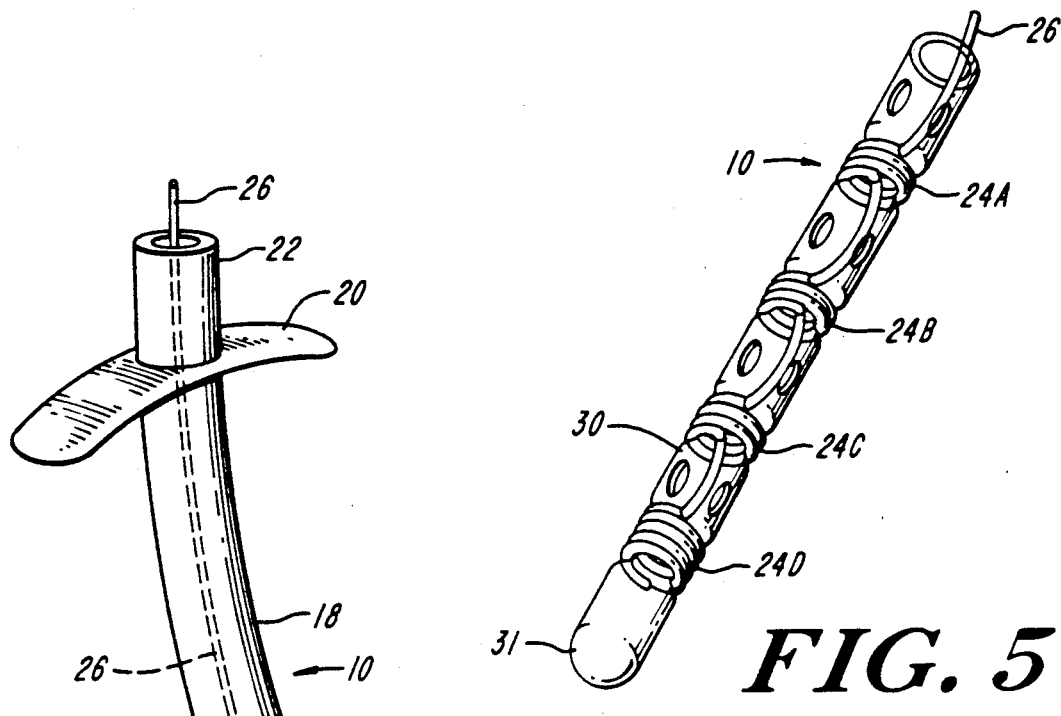
FIG. 5 is an enlarged perspective view of the distal end of the internal electrode shown in FIG. 4.

In FIG. 5, the distal end 30 of the electrode 10 is shown in detail. It includes four contact rings 24A-24D embedded in its surface. While four rings are shown, a lesser or greater number may be used. The contact rings in the embodiment shown are formed from a continuous length of tinned copper wire 26. The wire 26 extends inside the body 18 to first ring contact 24A, in turn formed by several turns of wire, on the surface of the body 18. The wire again enters the body 18 beyond the contact 24A and reemerges at the next ring contact 24B, also formed by several additional turns of wire. The third and fourth ring contacts 24C and 24D are similarly formed and connected to one another by the wire inside the body. Thus, the four electrode contacts are connected in series and formed from a single length of wire. Typically, each of the ring contacts may be 0.2-inch in axial length, and they may be spaced one inch apart. The wire may typically be 24-gauge The distal end 30 of the body is provided with a smooth, rounded tip 31 which will slide smoothly down the esophagus or guide tube (if used).

When the electrode 10 is used to defibrillate the heart, the distal end 30 is positioned so that the several ring contacts 24 lie in the lower third of the esophagus intimate to the posterior section of the heart H. The stop 20 insures proper positioning of the electrode.

The external electrode 12 may be like those used in electrocardiogram machines. As shown in FIG. 4, the electrode includes a flat, circular pad 32. A conducting gelatin is applied to the pad 32 when used to make good electrical contact with the patient's skin. The under surface of the pad 32 may also carry an adhesive to secure the electrode in place on the patient's chest.

Figure 6:
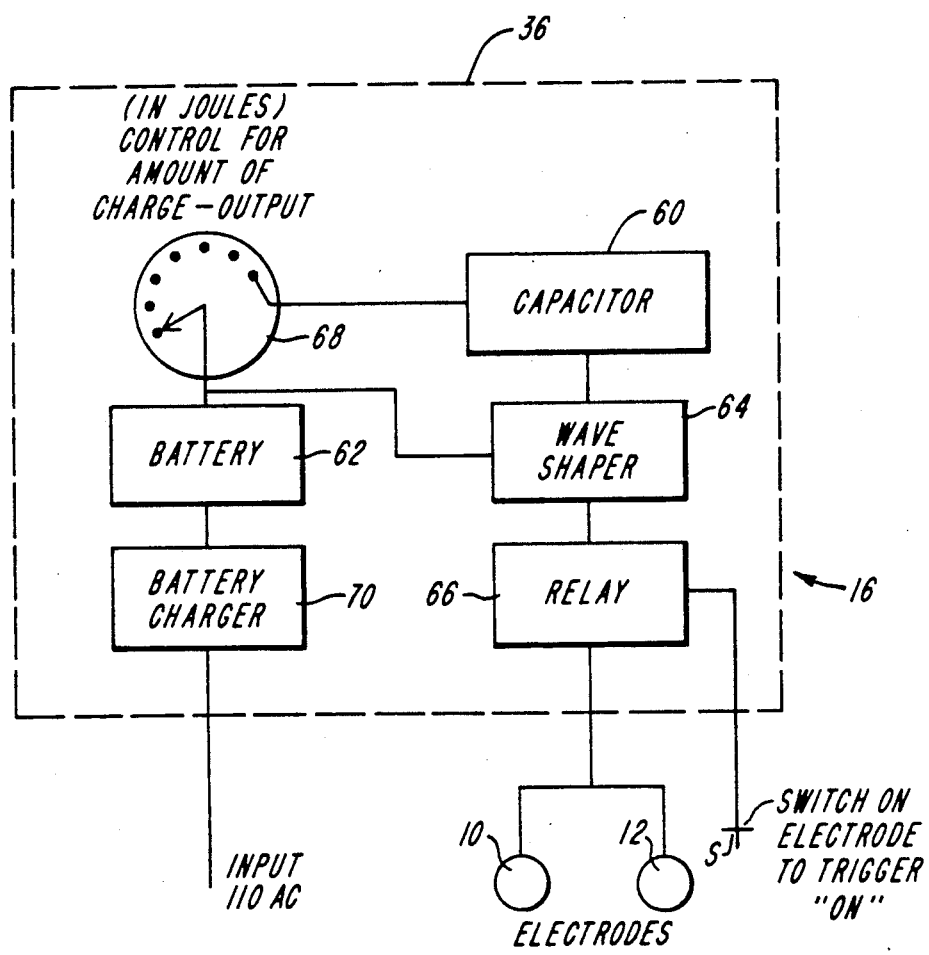
FIG. 6 is a box diagram of the electrical circuit connected to the electrode to supply the defibrillating pulse.

In FIG. 6, the electrodes are shown connected to a defibrillator 36 which represents any one of the many units now commercially available and capable of rendering a variable discharge. For use as part of the present invention, it must be capable of producing energy outputs (shock) in the 30-70 joules range. The unit may, of course, include a variety of display scopes, meters and recorders for indicating heart rate, electrocardiograph, available energy, energy selectors, etc. The unit shown has a capacitor 60, battery 62, wave shaper 64, switch controlled relay 66 and output control dial 68 for providing the energy output for defibrillation. Assuming the battery 62 is sufficiently charged, it will charge the capacitor 60 which in turn may be discharged by the switch controlled relay 66. The switch controlling the relay may be carried by external electrode 12. The battery may in turn be charged from a 110 volt source through the charger 70.

It is apparent that the several contact rings 24 on the internal electrode 10 are each capable of defining the electrical path to the externally applied electrode 12 so that the current of limited value will flow between them and through the heart. The contact ring 24 on the internal electrode which defines the path of least resistance with the electrode 12 placed on the chest will complete the electrical circuit.

Figure 2:
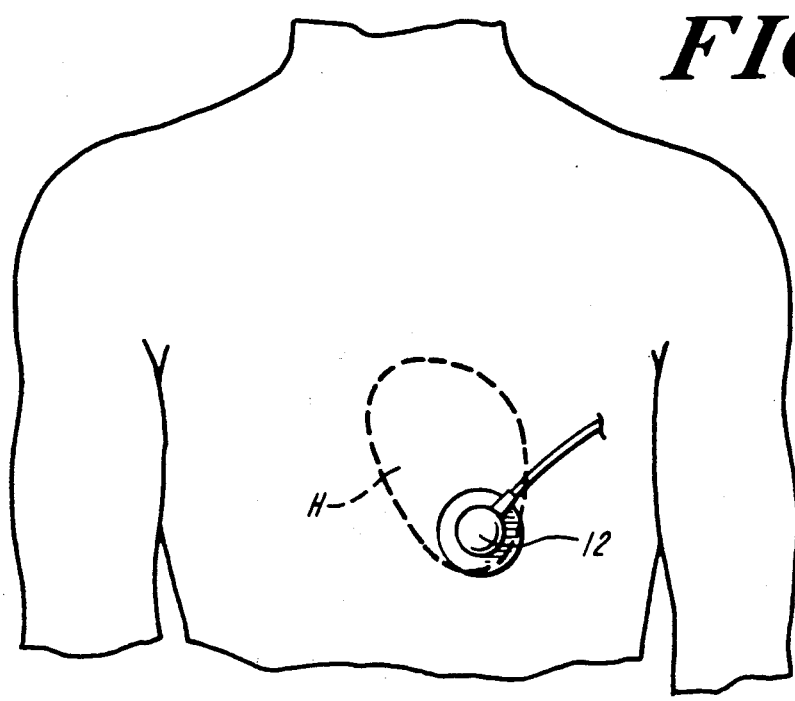
FIGS. 2 and 3 are plan views of a patient and showing the preferred precise placement of the external electrode on the chest to perform ventricular and atrial defibrillation, respectively.
Figure 3:
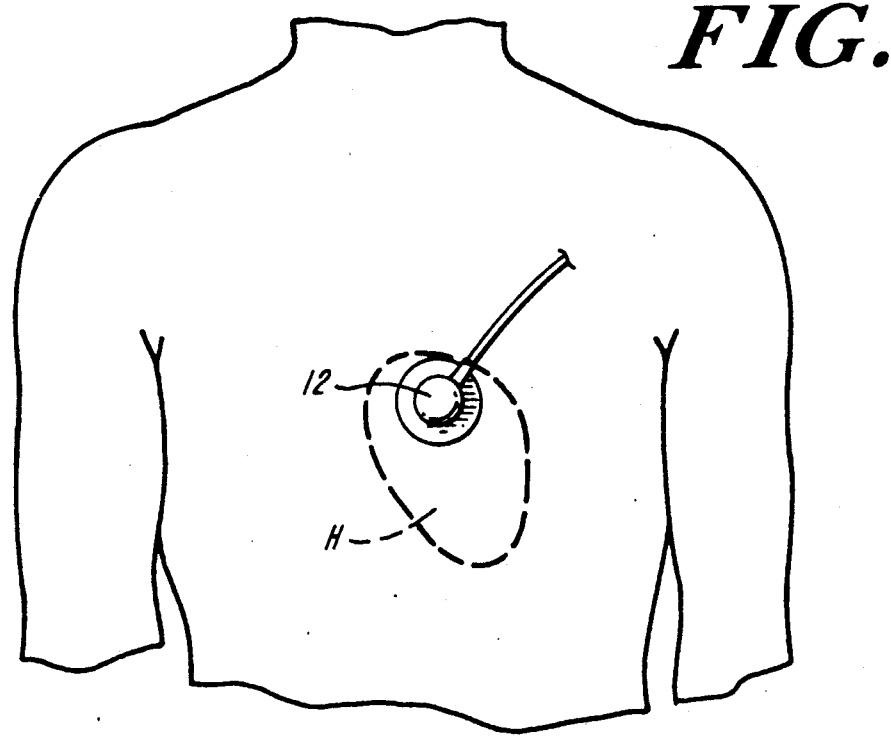

In FIGS. 2 and 3 the precise location for the placement of the external electrode is suggested for both atrial and ventricular defibrillation. In FIG. 3 which shows the placement of the external electrode for atrial defibrillation, electrode 12 is on a line between the nipples N of the patient, part way between the sternum and the left nipple. In FIG. 2, the external electrode 12 is shown placed above the apex of the left ventrical. With that placement, the electrical path between the inner and outer electrodes passes directly through the left ventrical. In the case of each type of defibrillation, the minimum electrical resistance encountered enables minimum energy to be used as an instantaneous discharge from presently available units. Tests have demonstrated that energy levels in the range of 30-100 joules are sufficient to defibrillate the heart and in most all instances a range of 30-70 is sufficient. This range is the same as is now used when defibrillation is achieved in open chest techniques where both electrodes are placed internally directly on the heart.

While the present invention permits the use of available defibrillators capable of reducing the energy discharge to 30-100 joules, it invites the manufacture and use of smaller and much less expensive defibrillators than those now available having ranges from 30-360 joules.

Having described the invention in detail, those skilled in the art will appreciate that numerous modifications may be made of it without departing from the spirit of this invention. Therefore, it is not intended that the breadth of this invention be limited to the specific embodiments illustrated and described. Rather, its scope is to be determined by the appended claims and their equivalents.

I claim:

1. A method of achieving atrial defibrillation of a patient's heart comprising the steps of
   placing a first electrode having at least one electrical contact internally in the lower third of the patient's esophagus,
   placing an electrode externally on the chest part way between the patient's left nipple and sternum and in alignment with the patient's nipples,
   and impressing an electrical pulse for defibrillation between the internal and external electrodes in the range of 30-100 joules.

2. A method of achieving ventricular defibrillation of the heart of a patient comprising the steps of
   placing a first electrode having at least one electrical contact internally in the lower third of the patient's esophagus,
   precisely placing an ECG-type electrode externally on the chest over the apex of the patient's left ventricle,
   and impressing an electrical pulse for defibrillation between the internal and external electrodes in the range of 30-100 joules.

3. A method of achieving atrial defibrillation of a patient's heart comprising the steps of
   placing a first electrode in the patient's esophagus,
   placing an electrode externally on the chest part way between the patient's left nipple and sternum and in alignment with the patient's nipples,
   and impressing an electrical pulse for defibrillation between the internal and external electrodes in the range of 30-100 joules.

4. A method of achieving ventricular defibrillation of a patient's heart comprising the steps of
   placing a first electrode in the patient's esophagus,
   precisely placing an electrode externally on the chest stationary with respect to the skin over the apex of the patient's left ventricle,
   and impressing an electrical pulse for defibrillation between the internal and external electrodes in the range of 30-100 joules.

5. A method of achieving atrial defibrillation of a patient's heart comprising the steps of
   placing a first electrode in the patient's esophagus,
   placing an electrode externally on the chest part way between the patient's left nipple and sternum and in alignment with the patient's nipples,
   and impressing an electrical pulse for defibrillation between the internal and external electrodes.

6. A method of achieving ventricular defibrillation of a patient's heart comprising the steps of
   placing a first electrode in the patient's esophagus,
   precisely placing an ECG-type electrode externally on the chest over the apex of the patient's left ventricle,
   and impressing an electrical pulse for defibrillation between the internal and external electrodes.

7. Apparatus for supplying an energy pulse to defibrillate the heart comprising
   an internal esophageal electrode means for placement in a patient's esophagus,
   an external electrode means for selective placement in fixed contact with the patient's skin for passing an electrical pulse through the apex of the patient's left ventricle to said esophageal electrode means,
   and an electrical energy source connected to both of the electrode for applying an electrical pulse between the electrodes in the range of 30 to 100 joules.

8. Apparatus for supplying an energy pulse to defibrillate the heart comprising
   an internal esophageal electrode means for placement in a patient's esophagus,
   an external electrode means for selective placement in fixed contact with the patient's skin for passing an electrical pulse through the patient's atria to said esophageal electrode means,
   and an electrical energy source connected to both of the electrode means for applying an electrical pulse between the electrode means in the range of 30 to 100 joules.

* * * * *